United States Patent [19]

Kuch

[11] Patent Number: 5,221,205
[45] Date of Patent: Jun. 22, 1993

[54] BRIDGE WITH LINGUAL BOLT LOCKING ATTACHMENT

[76] Inventor: Peter H. Kuch, 12180 SW. 131 Ave., Miami, Fla. 33186

[21] Appl. No.: 793,136

[22] Filed: Nov. 18, 1991

[51] Int. Cl.⁵ ..................... A61C 13/12; A61C 13/225
[52] U.S. Cl. ..................... 433/181; 433/182
[58] Field of Search .............. 433/181, 167, 172, 173, 433/182, 183, 193, 194

[56] References Cited

U.S. PATENT DOCUMENTS

| | | | |
|---|---|---|---|
| 2,127,285 | 8/1938 | Brecht | 433/182 |
| 2,411,001 | 11/1946 | Rothkranz | 433/182 |
| 2,572,714 | 10/1951 | Funderburg, Jr. | 433/174 |
| 3,820,241 | 6/1974 | Lasky | 433/181 |
| 3,866,321 | 2/1975 | Valen | 433/174 X |
| 4,085,506 | 4/1978 | Lew | 433/173 X |
| 4,746,295 | 5/1988 | Kipp | 433/182 |
| 4,767,328 | 8/1988 | Branemark | 433/173 X |
| 4,863,382 | 9/1989 | Bookstaber | 433/172 |

FOREIGN PATENT DOCUMENTS

| | | | |
|---|---|---|---|
| 2408341 | 7/1979 | France | 433/173 |
| 8801489 | 3/1988 | PCT Int'l Appl. | 433/173 |
| 9100711 | 1/1991 | PCT Int'l Appl. | 433/174 |
| 387224 | 5/1965 | Switzerland | 433/172 |

*Primary Examiner*—Gene Mancene
*Assistant Examiner*—Nicholas D. Lucchesi
*Attorney, Agent, or Firm*—Beveridge, DeGrandi, Weilacher

[57] ABSTRACT

Disclosed is a bridge which includes a subframe which is provided with a first engaging device, an overcast which is provided with a second engaging device and a locking element which cooperates with the first and second engaging devices to removably affix the overcast onto the subframe. Once the subframe has been anchored to the jaw of a patient, the overcast can be easily unlocked and removed from the subframe without removing the locking element from the overcast.

15 Claims, 3 Drawing Sheets

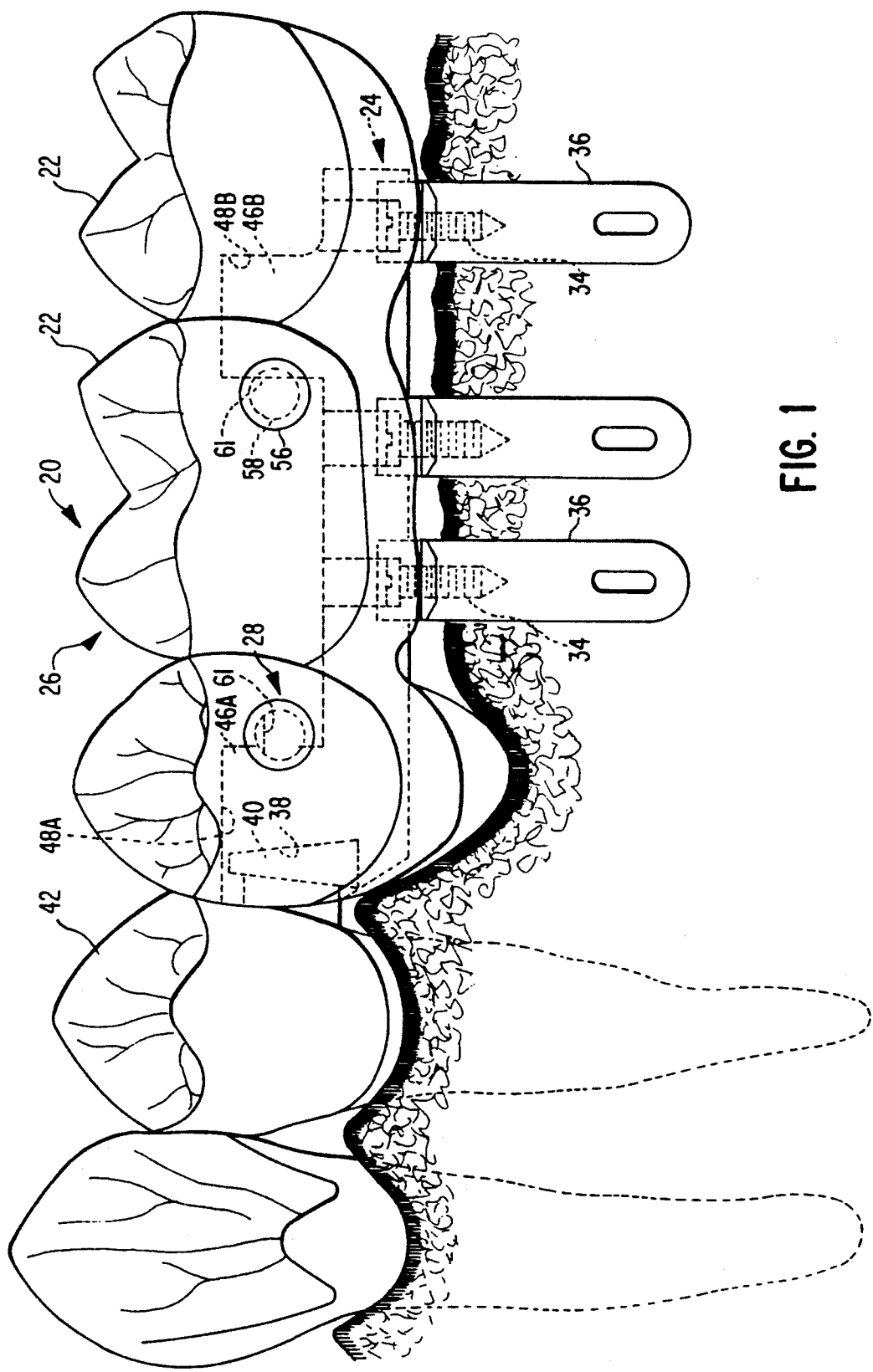

BRIDGE WITH LINGUAL BOLT LOCKING ATTACHMENT

BACKGROUND OF THE INVENTION

The present invention relates to a dental bridge. More particularly, the present invention relates to a bridge comprising an overcast which can be installed and removed easily from a subframe anchored to the jaw of a patient.

The prior art has recognized that it is desirable that bridges, when mounted in the mouth, be rigid to provide a firm and uniform bite. The advantages in providing a bridge which can be removed and reinstalled without destroying any portion of the bridge also have been noted. For instance, U.S. Pat. No. 3,442,015 discloses a rigidly mounted bridge which may be removed and reinstalled by the dentist for gum treatment without destroying the bridge, or disturbing crowned pier or abutment teeth adjacent the mounted bridge. U.S. Pat. No. 3,442,015 accordingly discloses mounting female members and male members in both a crowned portion of the pier teeth and in the end teeth of the bridge. Screws are installed through an opening which extends through the crown portions of the pier teeth, the female member and at least part way into the male member to fix the removable bridge to the pier teeth, over the patient's gum line.

The bridge disclosed in U.S. Pat. No. 3,442,015 however, requires that the pier teeth be ground down and that the crown having a corresponding male or female member be mounted on the ground pier teeth. The bridge thereafter is installed by fitting together the respective male and female members and installing the retaining bolts to lock the corresponding male and female members together. Removal of the bridge requires that the retaining bolts be at least partially withdrawn to permit separation of the male and female members.

SUMMARY OF THE INVENTION

The bridge in accordance with the present invention comprises a unitary subframe which is anchored to conventional inserts implanted in the jaw of the patient. The subframe has a base portion which rests upon the patient's gum line. Upstanding portions integrally formed with the base portion are provided with spaced-apart, opposing substantially planar surfaces which each have a notch therein. In the preferred embodiments, the notch is arcuate in cross-section and therefore forms a shoulder portion for each of the two upstanding portions.

Further in accordance with the present invention, an overcast is provided with recesses dimensioned to receive the upstanding portions of the subframe therein. Thus, the overcast telescopically fits onto the subframe and completely covers the subframe to provide a natural appearance for the overcast teeth. The overcast also is provided with at least one transversely-extending passage which communicates with the vertically-oriented recesses. The transversely-extending passage opens lingually and is aligned with the notches in the upstanding portions to receive retaining bolts therein. In the preferred embodiments, the retaining bolts have a head portion with threading which corresponds to a casting sleeve imbedded in the metallic central portion of an overcast tooth, and a generally-cylindrical shank portion which has a cut-out section defining a flat wall section in the shank. When the retaining bolt is installed within the opening defined through both the overcast and the subframe, the retaining bolt can be rotated by less than 360° to turn the bolt to either a releasing position wherein the flat wall of the retaining bolt directly faces the notch, or a locking position wherein the flat wall faces away from the notch so that the shank abuts with the shoulder. Thus, the overcast can be removed from, or mounted on the subframe without removing, or even substantially removing the retaining bolts therefrom. The bolts remain in the overcast to eliminate the possibility of their falling into the patient's mouth. In the releasing position, the shoulder may freely pass through the cut-out section of the retaining bolt to allow the overcast to be slid upwardly, off of the subframe. It also is contemplated that a retaining bolt having a fully cylindrical shank can be provided in order to prevent removal of the overcast without removal of the bolts.

The bridge in accordance with the present invention is arranged so that the overcast can be quickly and easily removed from the anchored subframe. The overcast can thus be cleaned or repaired as necessary without need for removing the subframe. Moreover, if it is required to also remove the subframe, the dentist needs only to remove the overcast and then the fastening means which anchors the subframe to the jaw implants. There is no need to remove conventional filler materials which are typically used to fill screw holes in prior art bridges because the overcast completely covers the subframe and thus obviates filler materials for the subframe.

To install the bridge in accordance with the present invention, insert posts are implanted in the patient's jaw, and then the subframe is anchored to the jaw inserts by conventional fastening means. Thereafter, the overcast is fitted onto the subframe and the retaining bolts are inserted lingually, into an opening defined by the fitted overcast and subframe to lock the overcast and subframe together. No modification of abutting or "pier" teeth is required. The bridge in accordance with the present invention provides increased strength to resist loosening of the overcast due to lateral forces occurring during chewing action by the patient. Even when the locking connection between the overcast and the subframe is loosened by lateral forces, the overcast again can be quickly and easily tightened to the subframe by a minor adjustment to the retaining bolts.

A bridge in accordance with the present invention comprises a unitary subframe which is arranged to be anchored to the jaw of a patient, on the patient's gum line, and which is provided with a first engaging means, an overcast arranged to fit onto the subframe and which is provided with a second engaging means, and locking means which cooperates with the first and second engaging means to removably affix the overcast means onto the subframe.

Also a method of installing a bridge on the gum line of a patient in accordance with the present invention comprises the steps of:

providing a unitary subframe to have two upstanding portions connected by a base portion, each of the upstanding portions defining a transversely extending shoulder portion;

anchoring the subframe to the jaw of a patient on the patient's gum line;

providing an overcast with an axially-oriented recess adapted to receive the upstanding portions of the subframe, and a transverse recess having a lingual opening;

placing the overcast onto the subframe so that the shoulder aligns with upper walls of the transverse recess; and installing an insertable member into the transverse recess and beneath the shoulder to affix the overcast onto the subframe.

BRIEF DESCRIPTION OF THE DRAWINGS

Further aspects and features of the present invention will be even more apparent from the following detailed description and drawings, and the appended claims. In the drawings:

FIG. 1 is a perspective view of a bridge in accordance with the present invention;

DETAILED DESCRIPTION OF THE PREFERRED EMBODIMENTS

Figure 2:
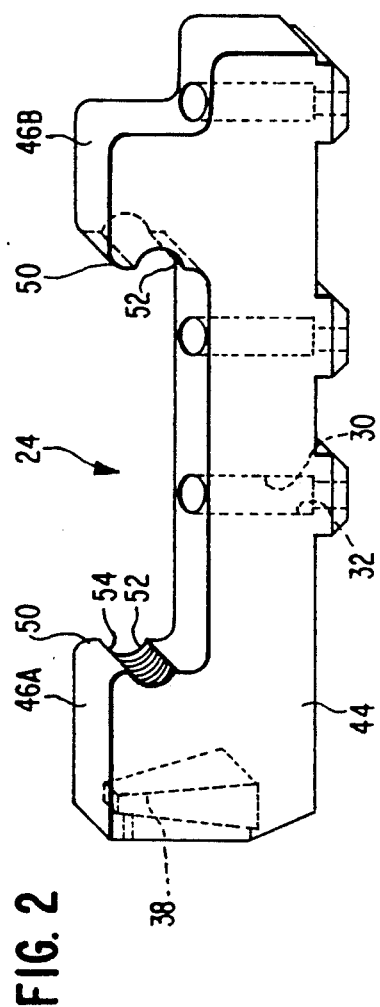
FIG. 2 is a perspective view of a sub frame for the bridge of FIG. 1.

With reference to FIGS. 1 and 2, a bridge 20 in accordance with the present invention is shown as providing three overcast teeth 22. Bridge 20 comprises a unitary subframe 24 that is adapted to be anchored to the jaw of the patient, an overcast 26, and retaining bolts 28 for removably securing the overcast to the mounted subframe. Subframe 24 and overcast 26 are fabricated with conventional materials using well-known casting methods. FIG. 2 is a perspective view of the subframe 24. Subframe 24 has three vertically-oriented receiving holes 30 which are countersunk to provide a portion 32 for threaded screws 34 which secure the subframe to implants 36 in the patient's jaw. Overcast 26 optionally can be provided with a pyramid shaped recess 38 for receiving a similarly shaped conventional pyramid member 40 mounted on a pier tooth 42 adjacent to the bridge 20.

Subframe 24 has a base portion 44 which rests upon the gum line and through which the countersunk holes 30 extend. The subframe also has two portions 46A and 46B which upstand from the base 44 and are receivable within two similarly-dimensioned recesses 48A and 48B in the overcast 26. Overcast 26 thus substantially completely covers subframe 24 to provide a natural appearance. Moreover, as a result of this covering relationship, there is no need for the dentist to fill in receiving holes 30 with a conventional filling material after screws 34 have been fastened because the holes are completely covered by overcast 26. This simplifies removal and anchoring of the subframe 24 by obviating filling material. As best shown in FIG. 2, each upstanding portion 46A, 46B, has a sidewall 50 and a notch 52 provided in the sidewall 50. Preferably, the notch 52 is arcuate, in cross-section. Each notch 52 defines an upper shoulder 54 which provides an engaging means for the subframe 24. Shoulders 54 cooperate with corresponding engaging means provided in the overcast 26. As will be discussed further in detail in the following, engaging means for the overcast are provided by arcuate, transversely-extending openings (not shown in FIG. 1) in the overcast 26. These transversely-extending openings (not shown in FIG. 1) also have an arcuate cross-section so as to define a passage with the notches 52 which is substantially circular in cross-section when the overcast 26 is fitted upon the subframe 24.

Figure 3:
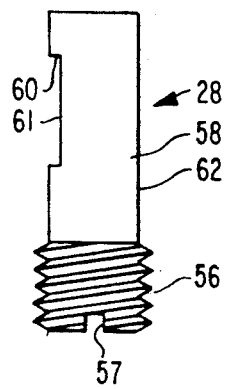
FIG. 3 is an elevational view of a preferred retaining bolt suitable for use in the bridge of FIG. 1.

With reference to FIG. 3, retaining bolts 28 are shown to include a threaded head portion 56 having a screw-slot 57 and a generally cylindrical shank portion 58. Shank portion 58 in turn has a cut-out section 60 which defines a flat wall 61 and thus a clearance. With reference also to FIG. 1, two retaining bolts 28 are shown as installed in bridge 20. The left-most bolt 28 is depicted as in its locked position so that the cylinder-like wall portions 62 are received within notch 52. As such, the overcast 26 can not be removed from the mounted subframe 24 because the walls 62 abut with shoulder 54. The right-most bolt 28 is depicted in a release position wherein its cut-out section 60 faces notch 52 of upstanding portion 46B. Due to the clearance provided by cut-out section 60, the bolt 28 could be moved upwardly past the shoulder 54 of upstanding portion 46B.

Figure 4:
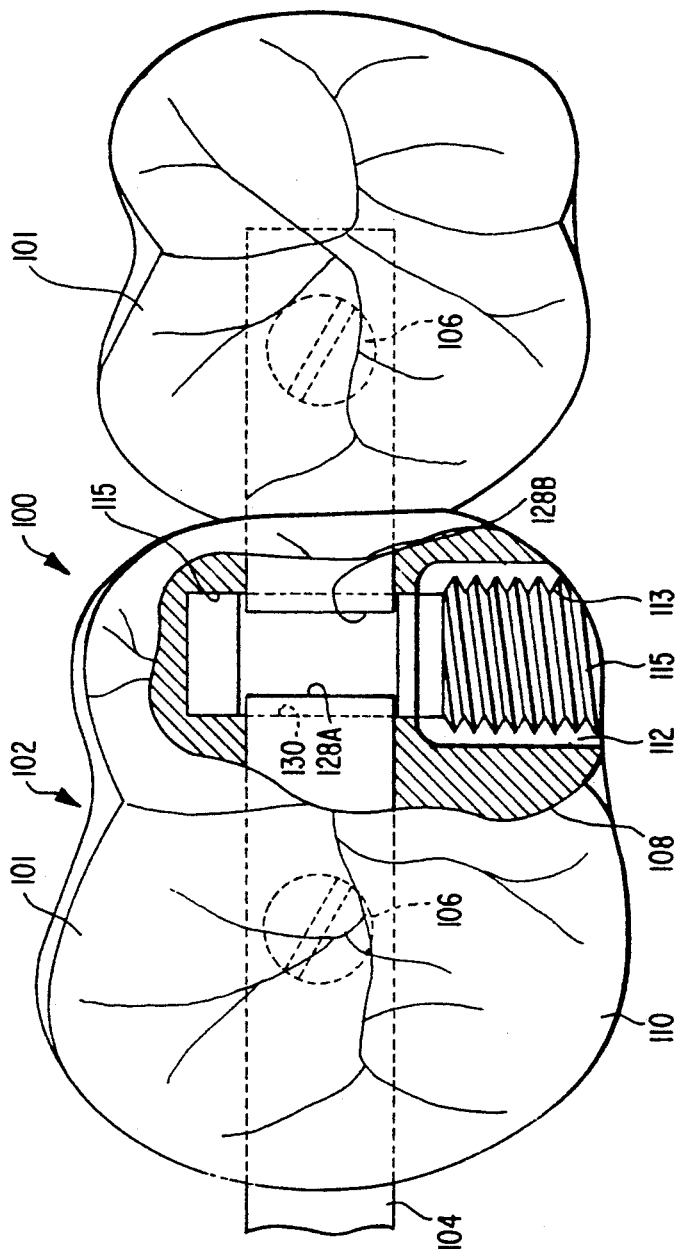
FIG. 4 is a downwardly-looking view of an alternative configuration for a bridge in accordance with the present invention.
Figure 5:
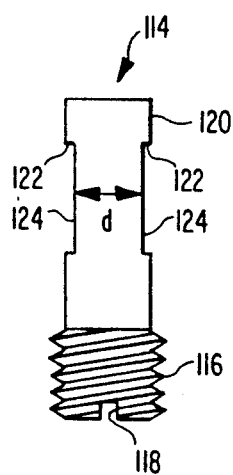
FIG. 5 is an elevational view of an alternative embodiment of a retaining bolt which is particularly suited for use in the bridge shown in FIG. 4.

FIG. 4 shows an alternative configuration of a bridge 100 which is arranged to provide two overcast teeth 101. A portion of the bridge subframe 104 is shown in broken lines in FIG. 4 together with its mounting screws 106 for anchoring subframe 104 to the patient's jaw. In FIG. 4, overcast 102 also is shown to comprise a metal interior 108 which is conventionally covered by an enamel layer 110. Preferably, a cast sleeve 112, which opens lingually, is provided in the metal 108 to provide threaded walls 113 which correspond with those of a retaining bolt 114 shown in elevational view in FIG. 5. Sleeve 112 forms a first section of the transversely-extending passage 115 in overcast 102. Retaining bolt 114 likewise comprises a threaded head portion 116 having a slot 118, and a generally cylindrical shank portion 120. Shank portion 120 has two opposing cut-out sections 122 defining substantially parallel substantially flat sidewalls 124 and thus clearances on opposite sides of the bolt 114.

Figure 6A:
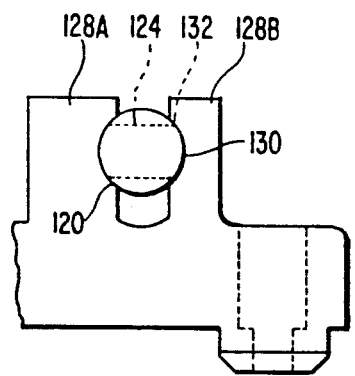
FIGS. 6A and 6B are sectional views showing the relationship between the sub frame and the retaining bolt in the bridge of FIG. 4.
Figure 6B:
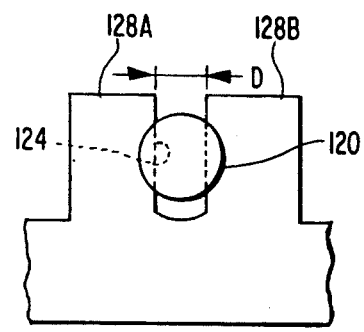

With reference also to FIGS. 6A and 6B, the engaging relationship of retaining bolts 114 and subframe 104 is particularly illustrated. Subframe 104 likewise includes two upstanding portions 128A, 128B provided with notches 130 therein to form shoulders 132 in each upstanding portion. Upstanding portions 128A, 128B are spaced apart a distance D which is slightly larger than the distance d through the cross section of shank 120, between sidewalls 124 thereof. Thus, when bolt 114 is rotated to the position shown in FIG. 6A, the overcast 106 is unlocked from subframe 104 whereby shoulders 132 pass through cut-out sections 122 so that the overcast can slide upwardly on upstanding portions 128 for removal. On the other hand, when bolts 114 are rotated to the position shown in FIG. 6B, the semicircular side walls 136 of bolts 114 engage shoulders 132 to securely fasten overcast 106 onto subframe 104.

In the preferred embodiments, the screw-slot 118 is provided to define a plane which generally will be either in parallel with, or perpendicular to, the flat walls 124 so that the dentist can determine whether the retaining bolt 114 is locked or unlocked merely by inspecting the position of the slot. As is apparent, bolt 114 can be turned between its locking and releasing positions without rotating it more than 360°. Thus the penetration of the bolt within notches 130 and within sleeve 113 does not substantially change when the bolt is turned between the locking and release positions. As such, the overcast 106 can be mounted on or removed from the subframe 104 without need for removing, or even partially removing bolt 114. The bolt 114 will remain within the overcasting 102 as it is removed.

Figure 7:
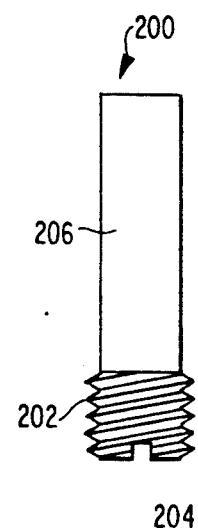
FIG. 7 is an elevational view of another retaining bolt in accordance with the invention.

Bolts 28 in connection with the embodiment of FIGS. 1 and 2, and double cut-out bolts 114 provided in connection with the embodiment of FIGS. 4, 5, 6A and 6B, are understood to provide an easily removable means for locking the overcast of each embodiment onto its corresponding subframe. As understood, in both of these embodiments, the bolts are rotatable between a locking position wherein their semicircular sidewalls are received within the notches of the subframe to thereby engage the shoulders, and a releasing position wherein a flat, sidewall of the bolts are aligned in a plane substantially parallel with the plane of the opposing sidewalls of the upstanding portions. It is also contemplated that for permanent locking of the overcast onto the subframe, bolt 200 shown in FIG. 7 can be used. Bolt 200 simply comprises a threaded head portion 202 having a slot 204, and a cylindrical shank portion 206. It is understood that once bolt 200 is installed within the transverse opening defined by cast sleeve 112, metal portion 108, and upstanding portions 128, the overcast 106 will be secured to subframe 104 until the bolts 200 are removed.

Figure 8:
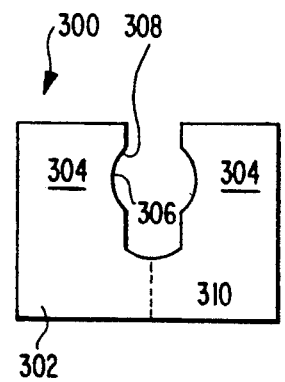
FIG. 8 is an elevational view of a molded sub frame suitable for use with the bridge in accordance with the present invention.

FIG. 8 shows a preferred blank 300 for forming a subframe in accordance with the present invention. Subframe blank 300 is a single-piece member comprising a base portion 302 and upstanding portions 304. Upstanding portions 304 likewise have arcuate notches 306 therein to define shoulders 308. Once blank 300 is formed, it may be cut along the dashed line 310 for separation into left and right-half sections. Thereafter, a connective section of any desired length can be formed in any conventional manner to reconnect the left and right half sections in order to form a bridge of any required length, depending upon the number of overcast teeth to be provided. Further, end portions can be formed on the half sections to provide the countersunk holes 30 as shown in FIG. 2.

In use, the dentist implants the members 36 in the patient's jaw. It is understood that installation of the bridge in accordance with the present invention requires opening of the gums only once for implantation of elements 36. Thereafter, the subframe 104 is anchored to the implants 36 and thus the patient's jaw by conventional fasteners 106. Once the subframe 104 is fastened to the jaw, there is no need to fill the receiving holes as they will be completely covered by the overcast 102. Next, the overcast 102 is fitted onto the subframe 104 with the subframe upstanding portions 128A, 128B being received within the corresponding recesses (not shown in FIG. 4) of the overcast to bring notches 130 into alignment with lingually-opening passage 115 of the overcast. Thereafter a retaining bolt 114 is threadably inserted into lingually openings passage 115 and tightened. Bolt 114 is then rotated to appropriately align the slot 124 to place the bolt in its locked position to securely mount the overcast 102 to the subframe 104.

In order to remove overcast 102, bolt 114 is simply rotated to its release position, the bolt remains threadably secured within the overcast 102 to prevent it from dropping into the patient's mouth. The overcast 102 is simply pulled off from the subframe 104. If the subframe 104 also requires removal, it is removed by unscrewing fasteners 106. It is appreciated that if lateral forces generated by chewing slightly adjust the angular position of bolt 114, the bolt can quickly and easily be readjusted by the dentist.

It is to be understood that there can various changes and modifications to the preferred embodiments of the present invention disclosed herein, which changes and/or modifications may be made by one of ordinary skill in the art, but such would still fall well within the scope of the invention as set forth in the claims.

I claim:

1. A bridge comprising:
   a unitary subframe which is arranged to be anchored to the jaw of a patient, on the patient's gum line and, which is provided with a first engaging means;
   an overcast arranged to fit onto the subframe and which is provided with a second engaging means, one of the engaging means comprising a transversely-extending shoulder, the other of the engaging means having a transversely-extending recess opening lingually; and
   locking means which cooperates with the first and second engaging means to removably affix the overcast onto the subframe, the locking means comprising a member insertable through the recess to contact the shoulder;
   the insertable member being axially receivable in the recess and being rotatable therein without substantially changing the penetration of the insertable member within the recess, between a locking position wherein the insertable member is in contact with the shoulder to affix the overcast to the subframe, and a releasing position wherein the insertable member does not contact the shoulder whereby the overcast is removable from the subframe.

2. A bridge as claimed in claim 1, wherein the insertable member comprises a bolt having a cut-out section which allows the shoulder to pass therethrough when the bolt is in its releasing position.

3. A bridge as claimed in claim 2, wherein the locking position of the bolt is less than 360° from the releasing position thereof.

4. A bridge as claimed in claim 3, wherein the bolt has two opposing cut-out sections.

5. A bridge as claimed in claim 4, wherein portions of the walls defining the recess comprise screw threads and a portion of the bolt comprises corresponding screw threads for securing the bolt in the recess.

6. A bridge as claimed in claim 1, wherein the subframe comprises an upstanding portion which defines the shoulder, and the overcast has an axially-oriented recess for receiving the upstanding portion and aligning the shoulder with the walls of the transversely-extending recess to permit insertion of the insertable member through the transversely-extending recess and beneath the shoulder.

7. A bridge as claimed in claim 6, wherein the shoulder is formed by an arcuate notch in the upstanding portion.

8. A bridge as claimed in claim 7, wherein the subframe has two upstanding portions, and the overcast has two axially-oriented recesses corresponding to the upstanding portions.

9. A bridge as claimed in claim 8, wherein the subframe has a vertically oriented recess adapted to receive a fastening means to anchor the subframe to a patient's jaw.

10. A bridge as claimed in claim 9, wherein the overcast substantially covers the subframe.

11. A bridge as claimed in claim 7, wherein the second engaging means of the overcast comprises a cast sleeve that forms a section of the transversely-extending recess and that has threaded interior walls, and wherein the insertable member comprises a bolt having a threaded portion formed to threadably engage the interior walls of the sleeve.

12. A method of installing a bridge on the gum line of a patient, said method comprising the steps of:
providing a unitary subframe to have two upstanding portions connected by a base portion, each of the upstanding portions defining a transversely extending shoulder;
anchoring the subframe to the jaw of a patient on the patient's gum line;
providing an overcast with an axially-oriented recess adapted to receive the upstanding portions of the subframe, and a transverse recess having a lingual opening;
placing the overcast onto the subframe so that the shoulder of at least one of the upstanding portions aligns with upper walls of the transverse recess; and
installing an insertable member into the transverse recess and beneath the shoulder of the at least one upstanding portion to affix the overcast onto the subframe.

13. A method as set forth in claim 12, wherein said step of providing the subframe comprises the steps of:
transversely cutting through the base portion of a subframe blank to provide two half sections; and
reconnecting the half sections to provide a subframe having a predetermined longitudinal length.

14. A method as set forth in claim 12, wherein the insertable member comprises a bolt which has a shank with a cut-out section therein, said method further comprising the steps of rotating the bolt in the transverse recess to a locking position wherein the shank contacts the shoulder of the at least one upstanding portion.

15. A method as set forth in claim 14, wherein detachment of the overcast from the subframe comprises the step of rotating the bolt to a releasing position wherein the cut-out section faces the shoulder of the at least one upstanding portion.

* * * * *